United States Patent [19]

Gerwick, III

[11] 4,447,257
[45] May 8, 1984

[54] INHIBITING THE ANTAGONISM BETWEEN PYRIDYLOXY-PHENOXY ALKANOATE HERBICIDES AND BENZOTHIADIAZINONE HERBICIDES IN POST-EMERGENT APPLICATIONS

[75] Inventor: Ben C. Gerwick, III, Concord, Calif.

[73] Assignee: The Dow Chemical Company, Midland, Mich.

[21] Appl. No.: 321,352

[22] Filed: Nov. 16, 1981

[51] Int. Cl.³ .............................................. A01N 25/00
[52] U.S. Cl. ............................................ 71/91; 71/74; 71/DIG. 1
[58] Field of Search ........................ 71/DIG. 1, 91, 94

[56] References Cited

U.S. PATENT DOCUMENTS

| 3,041,336 | 6/1962 | Teufel | 260/243 |
|---|---|---|---|
| 3,217,001 | 11/1965 | Santilli et al. | 260/243 |
| 3,621,017 | 11/1971 | Zeidler et al. | 71/91 |
| 3,708,277 | 1/1973 | Zeidler et al. | 71/91 |
| 3,940,389 | 2/1976 | McKendry et al. | 71/91 |
| 3,997,322 | 12/1976 | Ratledge | 71/93 |
| 4,051,130 | 9/1977 | McKendry et al. | 544/11 |
| 4,116,672 | 9/1978 | McKendry et al. | 71/91 |
| 4,155,746 | 5/1979 | McKendry et al. | 71/91 |
| 4,213,774 | 7/1980 | Seburter et al. | 71/94 |

FOREIGN PATENT DOCUMENTS

| 0000483 | 2/1979 | European Pat. Off. . |
| 7800008 | 3/1979 | United Kingdom . |
| 1550574 | 8/1979 | United Kingdom . |
| 2015995A | 9/1979 | United Kingdom . |

OTHER PUBLICATIONS

Research Disclosure, Feb. 1981, 20220, pp. 72–73.

*Primary Examiner*—Catherine L. Mills
*Attorney, Agent, or Firm*—John M. Sanders

[57] ABSTRACT

The addition of crop oil to herbicidal compositions containing pyridyloxy-phenoxy alkanoate herbicides and benzothiadiazinone herbicides inhibits the antagonism between the pyridyloxy-phenoxy alkanoate herbicides and the benzothiadiazinone herbicides.

20 Claims, No Drawings

INHIBITING THE ANTAGONISM BETWEEN PYRIDYLOXY-PHENOXY ALKANOATE HERBICIDES AND BENZOTHIADIAZINONE HERBICIDES IN POST-EMERGENT APPLICATIONS

BACKGROUND OF THE INVENTION

The present invention relates to inhibiting the antagonism between pyridyloxy-phenoxy alkanoate herbicides and benzothiadiazinone herbicides when applied post-emergently in compositions containing both classes of herbicides.

Pyridyloxy-phenoxy alkanoate derivatives, such as, for example, those described in Belgium Pat. No. 868,875; PCT Application WP No. 7900094; EPO Application No. 483; U.S. Pat. No. 4,213,774; and French Pat. No. 7522436, are useful as herbicides and are especially effective for selectively controlling annual and perennial grassy weeds in the presence of desirable broadleaf plants.

Benzothiadiazinone derivatives, described in U.S. Pat. Nos. 4,015,130; 4,116,672; 4,155,746; 3,940,389; 3,708,277 and 3,621,017 are useful as herbicides and especially as broadleaf active herbicides.

Pyridyloxy-phenoxy alkanoate herbicides are typically applied post-emergently in the presence of non-ionic surfactants. To extend the weed control spectrum in a given application, pyridyloxy-phenoxy alkanoate herbicides are mixed with benzothiadiazinone broadleaf active herbicides and thereafter applied to unwanted vegetation as a broad spectrum herbicidal composition effective against grasses and broadleaf weeds. The herbicidal activity to grasses of such mixtures is less than when pyridyloxy-phenoxy alkanoate herbicides are applied alone. Because of this antagonism in activity, it is necessary to increase the amount of the pyridyloxy-phenoxy alkanoate component in such mixtures to obtain equivalent grass control comparable to lesser amounts of pyridyloxy-phenoxy alkanoates when applied alone.

It is, therefore, desirable to provide a method for inhibiting the antagonism between pyridyloxy-phenoxy alkanoate herbicides and benzothiadiazinone herbicides when such herbicides are combined for post-emergent application to undesirable vegetation.

SUMMARY OF THE INVENTION

Briefly, in accordance with the present invention, the antagonism between pyridyloxy-phenoxy alkanoate herbicides and benzothiadiazinone herbicides is inhibited, when the herbicides are applied post-emergently in a composition containing (1) at least one pyridyloxy-phenoxy alkanoate herbicide and (2) at least one benzothiadiazinone herbicide, by the addition of an effective amount of a crop oil or crop oil concentrate to said composition.

The present invention also is directed to herbicidal compositions comprising (a) a pyridyloxy-phenoxy alkanoate herbicide, (b) a benzothiadiazinone herbicide and (c) an amount of crop oil effective to inhibit the antagonism between said pyridyloxy-phenoxy alkanoate herbicide and said benzothiadiazinone herbicide.

DETAILED DESCRIPTION

The crop oil component of the present invention is a petroleum distillate product containing primarily paraffinic and naphthenic hydrocarbons and generally containing less than 25 percent by weight aromatics. Such crop oils are known compounds which are disclosed in U.S. Pat. No. 3,997,322 which is incorporated herein by reference. Crop oils are non-phytotoxic and generally have the following range of properties:

| | |
|---|---|
| Gravity, °API/60° F. | 31.0–36.0 |
| Viscosity, SUS/100° F. | 60–120 |
| Viscosity, SUS/210° F. | 34–38 |
| Flash point, °F. | 300–400 |
| Fire point, °F. | 375–400 |
| Pour temperature, °F. | −10 to +20 |
| Unsulfonated residue, wt. percent (ASTM) | 75.0–99.9 |
| Refractive index, 25° C. | 1.4660–1.4690 |
| Gel aromatics, wt. percent, max. | 25.0 |
| Distillation range at 10 mm. HG (ASTM D-1160) | 300–500 |

The term "crop oil" when used herein is meant to encompass crop oil concentrates. A crop oil concentrate is a crop oil which contains more surfactants or emulsifiers than a "crop oil". A crop oil concentrate typically contains surfactants or emulsifiers in amounts of up to about 30 percent by weight while a crop oil generally contains less than 5 percent by weight of surfactants or emulsifiers.

In the practice of the present invention an effective amount of a crop oil is added to a herbicidal spray composition containing a pyridyloxy-phenoxy alkanoate herbicide and a benzothiadiazinone herbicide whereby said crop oil inhibits the antagonism between said herbicides. Generally, an effective amount of a crop oil constitutes at least about 0.1 percent by volume of the total herbicidal composition. Advantageously, the crop oil is present in an amount of from about 0.25 to about 5 percent by volume of the total composition and preferably from about 0.5 to about 1.5 percent by volume of the total composition.

Crop oils are well known compositions and are commercially available. Suitable crop oils employed in the practice of the present invention include crop oils, crop oil concentrates and blends of crop oils with emulsifying agents, such as, for example: Sun ® 11-E; Atplus ® 411-F; Booster ® Plus E; Agri-Oil ® Plus; Agri Dex ®; Agrodex ®; Herb-Oil ® Plus; U.S.S. Spray Adjuvant ®; Agicide Activator ®; Prime Oil ®, Crop Surf ® Spray Oil; Adjucide ®; Mor-Act ®; Sunoco ® Superior Spray Oils; Orchex ® 696; Paramid ® 100; and Sun ® Superior Spray Oils.

The pyridyloxy-phenoxy alkanoate herbicides of the present invention, generally grass active herbicides, are known compounds and include all of the compounds described in Belgium Pat. No. 868,875; PCT Application WP No. 7900094; EPO Application 483; U.S. Pat. No. 4,213,774 and French Pat. No. 7522436 all of which are incorporated herein by reference. Preferred pyridyloxy-phenoxy alkanoate herbicides include pyridyloxy-phenoxy propionate compounds of the formula

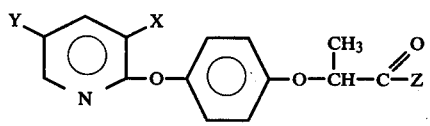

wherein
X represents hydrogen, halo or —CF$_3$;
Y represents halo or —CF$_3$; and
Z represents: —OH and alkaline earth metal and alkali metal salts thereof; 1–18 C alkoxy optionally substituted with up to 3 halo groups, a 1–6 C alkoxy or a 1–4 C alkoxy carbonyl; 2–8 C alkenyloxy; 2–8 C alkynyloxy; 3–12 C cycloalkyloxy optionally substituted with a 1–4 C alkyl; phenoxy optionally substituted with up to 3 halo groups, a 1–4 C alkyl or a 1–4 C alkoxy; benzyloxy with the phenyl group optionally carrying up to 3 halo or methyl groups; 1–18 C alkylthio; phenylthio, the phenyl moiety being optionally substituted with up to 3 halo groups, 1–4 C alkyl groups or 1–4 C alkoxy groups; amino; 1–4 C alkylamino; and anilino wherein then the phenyl moiety is optionally substituted with up to 3 halo groups, 1–4 C alkyl groups or 1–4 C alkoxy groups.

Specific pyridyloxy-phenoxy propionate herbicides within the scope of the present invention include:

2-(4-((5-(trifluoromethyl)-2-pyridinyl)oxy)phenoxy)-propanoic acid and salts thereof;

2-(4-((3-chloro-5-(trifluoromethyl)-2-pyridinyl)oxy)-phenoxy)propanoic acid and salts thereof;

methyl 2-(4-((5-(trifluoromethyl)-2-pyridinyl)oxy)-phenoxy)propanoate;

butyl 2-(4-((5-(trifluoromethyl)-2-pyridinyl)oxy)-phenoxy)propanoate;

ethoxy ethyl 2-(4-((5-(trifluoromethyl)-2-pyridinyl)oxy)phenoxy)propanoate;

1-methoxy-2-propyl 2-(4-((5-(trifluoromethyl)-2-pyridinyl)oxy)phenoxy)propanoate;

methyl 2-(4-((3-chloro-5-(trifluoromethyl)-2-pyridinyl)oxy)phenoxy propanoate;

butyl 2-(4-((3-chloro-5-(trifluoromethyl)-2-pyridinyl)oxy)phenoxy propanoate;

ethoxy ethyl 2-(4-((3-chloro-5-(trifluoromethyl)-2-pyridinyl)oxy)phenoxy propanoate; and 1-methoxy-2-propyl 2-(4-((3-chloro-5-(trifluoromethyl)-2-pyridinyl)oxy)phenoxy propanoate.

The pyridyloxy-phenoxy alkanoate herbicides of the present invention may exist in optically active stereoisomeric forms such as the dextrorotatory and levorotatory forms. The various mixtures and racemates of such isomers are within the scope of the present invention.

The benzothiadiazinone herbicides of the present invention, generally broadleaf active herbicides, are known compounds and include all of the compounds described in U.S. Pat. Nos. 4,051,130; 4,116,672; 4,155,746; 3,940,389; 3,708,277 and 3,621,017, all of which are incorporated herein by reference. Preferred benzothiadiazinone herbicides include those of the formula

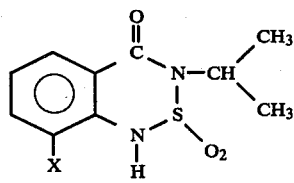

wherein

X represents hydrogen, chloro, bromo, fluoro, $C_1$–$C_8$ alkyl and nitro, and salts thereof.

Specifically preferred benzothiadiazinone herbicides include:

8-chloro-3-(1-methylethyl)-1H-2,1,3-benzothiadiazin-4(3H)-one-2,2-dioxide;

8-nitro-3-(1-methylethyl)-1H-2,1,3-benzothiadiazin-4(3H)-one-2,2-dioxide;

8-fluoro-3-(1-methylethyl)-1H-2,1,3-benzothiadiazin-4(3H)-one-2,2-dioxide;

8-methyl-3-(1-methylethyl)-1H-2,1,3-benzothiadiazin-4(3H)-one-2,2-dioxide; and 3-(1-methylethyl)-1H-2,1,3-benzothiadiazinone-4(3H)-one-2,2-dioxide, commonly known as bentazon.

Bentazon, a broadleaf active herbicide and a preferred compound, is a commercially available product from the BASF Wyandotte Corporation under the trade name BASAGRAN. Bentazon is usually applied to broadleaf weeds at a rate of from about 0.75 to about 2 lbs. of active ingredient per acre.

In the practice of the present invention the order of admixing the crop oil with the pyridyloxy-phenoxy alkanoate herbicide and the benzothiadiazinone herbicide is not critical. For example, the crop oil may be mixed with either herbicide alone and thereafter formulated into a spray formulation using well known techniques. Alternatively, the herbicides may be formulated into a spray formulation and then the crop oil may be added, with sufficient agitation, to disperse the crop oil uniformly throughout the formulation.

Once prepared the compositions of the present invention are applied to unwanted vegetation employing procedures well known in the art.

The following examples illustrate the present invention and the manner by which it can be practiced but, as such, are not to be construed as limitations upon the overall scope of the same.

EXAMPLE 1

2-(4-((3-chloro-5-(trifluoromethyl)-2-pyridinyl)oxy)-phenoxy)propanoic butyl ester, hereinafter referred to as active compound "A", formulated as an oil-in-water emulsion, was applied to *Setaria viridis*, 4 inch in height, with a belt-driven track sprayer calibrated to deliver 20 gallons/acre through an 8002 T-Jet nozzle. The herbicide was applied at rates of 0.25, 0.125, 0.063, 0.031 and 0.016 lbs/acre in the presence of either 0.25% v/v Colloidol ® X-77 brand non-ionic surfactant or 1.25% v/v Atplus ® 411-F brand crop oil concentrate. Bentazon, commercially available from BASF Wyandatte Corporation, as a Na+ salt formulation, was added to an identical series of active compound "A" emulsions and applied either in the presence of Colloidol ® X-77 brand non-ionic surfactant or Atplus ® 411-F brand crop oil. When bentazon was applied, it was applied at a rate of 0.75 lbs/acre. All applications were made and evaluated on 3 pots, each containing 3–5 plants.

Following herbicidal application, plants were maintained in a greenhouse and watered by subirrigation. After 14 days the degree of injury to *Setaria viridis* was visually assessed for growth retardation relative to untreated controls on a scale of 0–100, wherein "100" indicates complete kill or growth retardation and "0" indicates no growth retardation or no herbicidal effect.

"$ED_{80}$" listed in Table I means 80 percent of a totally effective dose. By this term it is meant to indicate the application rate, in lbs/acre, of a herbicide effective to kill or control 80 percent of the treated vegetation. For example, a herbicide having a $ED_{80}$ of 0.100 would indicate that the application of 0.100 lbs/acre of that particular herbicide would kill or control 80 percent of the treated vegetation. The results are listed in Table 1.

TABLE 1

| Treatment | Additives | Percent Kill and Control With Various Rates of Active Compound "A" (lbs/acre) | | | | | |
|---|---|---|---|---|---|---|---|
| | | 0.25 | 0.125 | 0.063 | 0.031 | 0.016 | $ED_{80}$ |
| 1 | Colloidal = x-77 | 100 | 90 | 90 | 10 | 0 | 0.075 |
| | (non-ionic surfactant) | 99 | 95 | 90 | 30 | 0 | |
| | | 99 | 95 | 60 | 40 | 0 | |
| 2 | Colloidal = x-77 (non-ionic | 99 | 85 | 20 | 0 | 0 | 0.159 |
| | surfactant) plus bentazon | 99 | 35 | 10 | 0 | 0 | |
| | (0.75 lbs/acre) | 85 | 85 | 40 | 0 | 0 | |
| 3 | Atplus = 411-F (crop oil) | 100 | 95 | 60 | 5 | 0 | 0.085 |
| | | 100 | 95 | 55 | 10 | 0 | |
| | | 99 | 90 | 85 | 15 | 0 | |
| 4 | Atplus = 411-F (crop oil) | 100 | 90 | 55 | 15 | 0 | 0.100 |
| | plus bentazon (0.75 | 99 | 95 | 50 | 10 | 0 | |
| | lbs/acre) | 99 | 85 | 40 | 20 | 0 | |

Similar results are achievable when other pyridyloxy-phenoxy alkanoate herbicides, benzothiadiazinone herbicides and crop oils, all of which are described herein, are employed as broad spectrum herbicidal compositions whereby the antagonism between the herbicides is inhibited.

EXAMPLE 2

A herbicidal spray composition was prepared by mixing the following:

| | |
|---|---|
| BASAGRAN ® | 0.75–2 lb. |
| 2-(4-((3-chloro-5-trifluoro-methyl)-2-pyridinyl)oxy)phenoxy)-propanoic butyl ester | 1/16–½ lb. |
| Crop oil | 0.02–1 gallon |
| Water | balance to 20 gallons |
| | 20 gallons |

The crop oil employed was Atplus ® 411 brand crop oil. The herbicides were supplied as liquid formulations. The BASAGRAN ® contained 4 lbs a.i./gal. The 2-(4-((3-chloro-5-trifluoromethyl)-2-pyridinyl)oxy)phenoxy)propanoic butyl ester, formulated in a 2 lb/gallon in xylene range petroleum distillate solvent, was mixed with the crop oil and water to form an emulsion. The BASAGRAN was thereafter added, with agitation, to complete the formulation. This formulation was then applied as a broad spectrum herbicide to one acre.

Spray Composition 1

A herbicidal spray composition, similar to that of Example 2, is prepared with the exception that 2-(4-((5-trifluoromethyl)-2-pyridinyl)oxy)phenoxy propanoic butyl ester is substituted for 2-(4-((3-chloro-5-(trifluoromethyl)-2-pyridinyl)oxy)phenoxy propanoic butyl ester.

Spray Composition 2

A herbicidal spray composition, similar to that of Example 2, is prepared with the exception that 8-fluoro-3-(1-methylethyl)-1H-2,1,3-benzothiadiazin-4(3H)-one-2,2-dioxide is substituted for BASAGRAN ®.

Spray Composition 3

A herbicidal spray composition, similar to Spray Composition 1, is prepared with the exception that 8-fluoro-3-(1-methylethyl)-1H-2,1,3-benzothiadiazin-4(3H)-one-2,2-dioxide is substituted for BASAGRAN ®.

Spray Composition 4

A herbicidal spray composition similar to those of Example 2 and Spray Compositions 1–3 is prepared where the crop oil employed is Atplus ® 411-F; Sun ® 11-E; Booster ® Plus E; Agri-Oil ® Plus; Agri-Dex ®; Agrodex ®; Herb-Oil ® Plus; U.S.S. Spray Adjuvant ®; Agicide Activator ®; Prime Oil ®; Crop Surf ® Spray Oil; Adjucide ®; Mor-Act ®; Sunoco ® Superior Spray Oils; Orchex ® 696; Paramid ® 100; Sun ® Superior Spray Oils or mixtures thereof.

In other representative operations, various pyridyloxy-phenoxy alkanoate herbicides, benzothiadiazinone herbicides and crop oils, all of which are described herein, are mixed in amounts within the scope of the present invention with water to form herbicidal spray compositions whereby the antagonism between the herbicides is inhibited.

In further embodiments, the broad spectrum herbicidal compositions of the present invention can be advantageously employed in combination with one or more additional pesticidal compounds. Such additional pesticidal compounds may be insecticides, nematocides, arthropodicides, herbicides, fungicides or bactericides that are compatible with the compositions of the present invention. Accordingly, in such embodiments, the pesticidal compound is employed as a supplemental toxicant for the same or for a different pesticidal use, or as an additament.

I claim:

1. A method of inhibiting the antagonism between pyridyloxy-phenoxy propionate herbicides and benzothiadiazinone herbicides of the formula

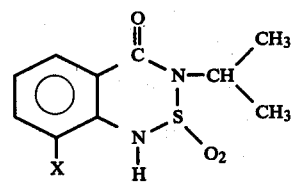

wherein
X represents hydrogen, chloro, bromo, fluoro, $C_1$–$C_8$ alkyl or nitro, and salts thereof, when applied post-emergently to unwanted vegetation in a composition containing both of said herbicides, said method comprising adding an amount of a non-phytotoxic petroleum distillate crop oil effective to inhibit the antagonism between the pyridyloxy-phenoxy propionate herbicide and the benzothiadiazinone herbicide.

2. The method of claim 1 wherein said crop oil is added in an amount of at least about 0.1 percent by volume of the total composition.

3. The method of claim 1 wherein said crop oil is added in an amount of from about 0.5 to about 5 percent by volume of the total composition.

4. The method of claim 1 wherein said crop oil is added in an amount of from about 0.5 to about 1.5 percent by volume of the total composition.

5. The method of claim 1 wherein said pyridyloxy-phenoxy propionate herbicide is 2-4-(-((3-chloro-5-(trifluoromethyl)-2-pyridinyl)oxy)phenoxy)propanoic acid, an ester or salt thereof and said benzothiadiazinone herbicide is bentazon.

6. The method of claim 5 wherein said benzothiadiazinone herbicide is:
8-chloro-3-(1-methylethyl)-1H-2,1,3-benzothiadiazin-4(3H)-one-2,2-dioxide;
8-nitro-3-(1-methylethyl)-1H-2,1,3-benzothiadiazin-4(3H)-one-2,2-dioxide;
8-fluoro-3-(1-methylethyl)-1H-2,1,3-benzothiadiazin-4(3H)-one-2,2-dioxide;
8-methyl-3-(1-methylethyl)-1H-2,1,3-benzothiadiazin-4(3H)-one-2,2-dioxide; salts thereof; or mixtures thereof.

7. The method of claim 1 wherein said pyridyloxy-phenoxy propionate herbicide is 2-(4-((5-(trifluoromethyl)-2-pyridinyl)oxy)phenoxy)propanoic acid, an ester or a salt thereof and said benzothiadiazinone herbicide is bentazon.

8. The method of claim 7 wherein said benzothiadiazinone herbicide is:
8-chloro-3-(1-methylethyl)-1H-2,1,3-benzothiadiazin-4(3H)-one-2,2-dioxide;
8-nitro-3-(1-methylethyl)-1H-2,1,3-benzothiadiazin-4(3H)-one-2,2-dioxide;
8-fluoro-3-(1-methylethyl)-1H-2,1,3-benzothiadiazin-4(3H)-one-2,2dioxide;
8-methyl-3-(1-methylethyl)-1H-2,1,3-benzothiadiazin-4(3H)-one-2,2-dioxide; salts thereof; or mixtures thereof.

9. In a broad spectrum herbicidal spray composition comprising
(a) at least one pyridyloxy-phenoxy propionate herbicide, and
(b) at least one benzothiadiazinone herbicide of the formula

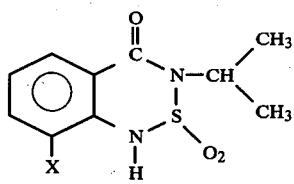

wherein
X represents hydrogen, chloro, bromo, fluoro, $C_1$–$C_8$ alkyl or nitro, and salts thereof, the improvement which comprises adding to said composition, non-phytotopic petroleum distillate a crop oil or a mixture of said crop oils in an amount effective to inhibit the antagonism between the pyridyloxy-phenoxy propionate herbicide and the benzothiadiazinone herbicide.

10. The composition of claim 9 wherein said crop oil is present in an amount of at least about 0.1 percent by volume.

11. The composition of claim 9 wherein said crop oil is present in an amount of from about 0.5 to about 5 percent by volume.

12. The composition of claim 9 wherein said crop oil is present in an amount of from about 0.5 to about 1.5 percent by volume.

13. The composition of claim 9 wherein said pyridyloxy-phenoxy propionate herbicide is 2-4(-((3-chloro-5-(trifluoromethyl)-2-pyridinyl)oxy)phenoxy)-propanoic acid, or an ester or salt thereof and said benzothiadiazinone herbicide is bentazon.

14. The composition of claim 13 wherein said benzothiadiazinone herbicide is:
8-chloro-3-(1-methylethyl)-1H-2,1,3-benzothiadiazin-4(3H)-one-2,2-dioxide;
8-nitro-3-(1-methylethyl)-1H-2,1,3-benzothiadiazin-4(3H)-one-2,2-dioxide;
8-fluoro-3-(1-methylethyl)-1H-2,1,3-benzothiadiazin-4(3H)-one-2,2-dioxide;
8-methyl-3-(1-methylethyl)-1H-2,1,3-benzothiadiazin-4(3H)-one-2,2-dioxide; salts thereof; or mixtures thereof.

15. The composition of claim 9 wherein said pyridyloxy-phenoxy propionate herbicide is 2-(4-((5-trifluoromethyl)-2-pyridyl)oxy)phenoxy)propanoic acid, an ester or a slat thereof and said benzothiadiazinone herbicide is bentazon.

16. The composition of claim 15 wherein said benzothiadiazinone herbicide is:
8-chloro-3-(1-methylethyl)-1H-2,1,3-benzothiadiazin-4(3H)-one-2,2-dioxide;
8-nitro-3-(1-methylethyl)-1H-2,1,3-benzothiadiazin-4(3H)-one-2,2-dioxide;
8-fluoro-3-(1-methylethyl)-1H-2,1,3-benzothiadiazin-4(3H)-one-2,2dioxide;
8-methyl-3-(1-methylethyl)-1H-2,1,3-benzothiadiazin-4(3H)-one-2,2-dioxide; salts thereof; or mixtures thereof.

17. The method of claim 7 wherein the pyridyloxy-phenoxy propionate herbicide is butyl 2-(4-((5-(trifluoromethyl)-2-pyridinyl)oxy)phenoxy)propionate and the crop oil is ATPLUS 411-F brand crop oil.

18. The composition of claim 15 wherein the pyridyloxy-phenoxy propionate herbicide is butyl 2-(4-((5-(trifluoromethyl)-2-pyridinyl)oxy)phenoxy)propionate and the crop oil is ATPLUS 411-F brand crop oil.

19. The method of claim 5 wherein the pyridyloxy-phenoxy propionate herbicide is ethoxyethyl 2-(4-((3-chloro-5-(trifluoromethyl)-2-pyridinyl)oxy)phenoxy)-propionate and the crop oil is ATPLUS 411-F brand crop oil.

20. The composition of claim 13 wherein the pyridyloxy-phenoxy propionate herbicide is ethoxyethyl 2-(4((3-chloro-5-(trifluoromethyl)-2-pyridinyl)oxy)-phenoxy)propionate and the crop oil is ATPLUS 411-F brand crop oil.

* * * * *